United States Patent [19]

Teraji et al.

[11] Patent Number: 4,550,102
[45] Date of Patent: Oct. 29, 1985

[54] CEPHEM COMPOUNDS

[75] Inventors: Tsutomu Teraji, Osaka; Kazuo Sakane, Amagasaki; Jiro Goto, Suita, all of Japan

[73] Assignee: Fujisawa Pharmaceutical Co. Ltd., Osaka, Japan

[21] Appl. No.: 415,910

[22] Filed: Sep. 8, 1982

[30] Foreign Application Priority Data

Sep. 14, 1981 [GB] United Kingdom ............... 8127664

[51] Int. Cl.[4] ................ C07D 501/38; A61K 31/545
[52] U.S. Cl. ........................................ 514/206; 544/25
[58] Field of Search .......................... 544/27, 25, 26; 424/246; 514/206

[56] References Cited

U.S. PATENT DOCUMENTS

| | | | |
|---|---|---|---|
| 4,237,128 | 12/1980 | Cimarusti et al. | 544/25 |
| 4,258,041 | 3/1981 | O'Callaghan et al. | 424/246 |
| 4,278,671 | 7/1981 | Ochiai et al. | 424/246 |
| 4,278,793 | 7/1981 | Durckheimer et al. | 544/25 |
| 4,394,503 | 7/1983 | Kamadu et al. | 544/25 |
| 4,407,798 | 10/1983 | Kamiya et al. | 544/25 |

Primary Examiner—Nicholas S. Rizzo
Attorney, Agent, or Firm—Oblon, Fisher, Spivak, McClelland & Maier

[57] ABSTRACT

The invention relates to novel cephem compounds of high antimicrobial activity of the formula:

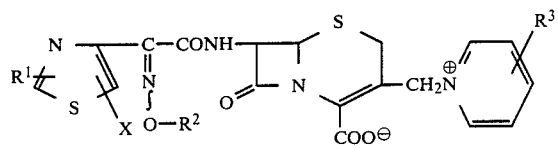

wherein
$R^1$ is amino or lower alkanoylamino,
$R^2$ is lower alkyl, lower alkynyl, carboxy (lower) alkyl or esterified carboxy (lower) alkyl,
$R^3$ is amino or lower alkanoylamino, and
X is hydrogen or halogen; and pharmaceutically acceptable salts thereof.

9 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

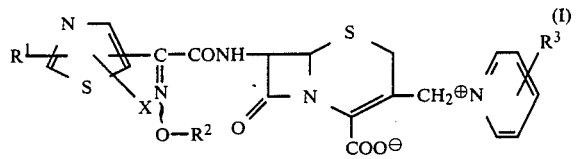

(I)

wherein
$R^1$ is amino or a protected amino group;
$R^2$ is lower aliphatic hydrocarbon group which may have suitable substituent(s);
$R^3$ is amino or a protected amino group; and
X is hydrogen or halogen.

According to the present invention, the new cephem compounds (I) can be prepared by various processes which are illustrated in the following scheme.

Process 1

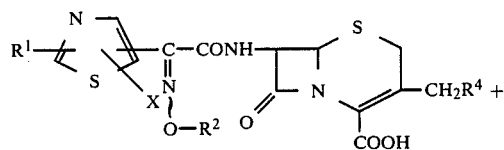

(II)
or a salt thereof

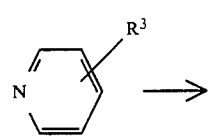

(III)
or a salt thereof

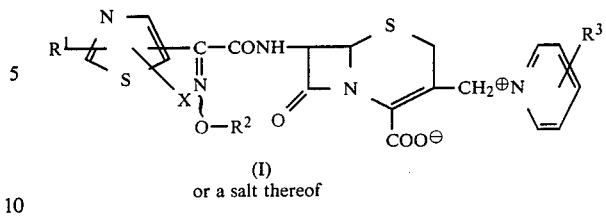

(I)
or a salt thereof

Process 2

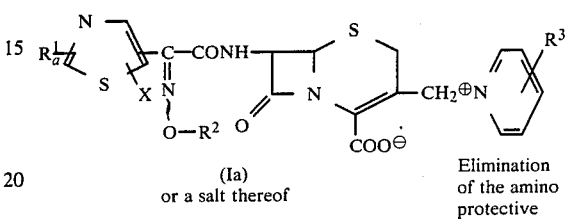

(Ia)
or a salt thereof

Elimination of the amino protective group ⟶

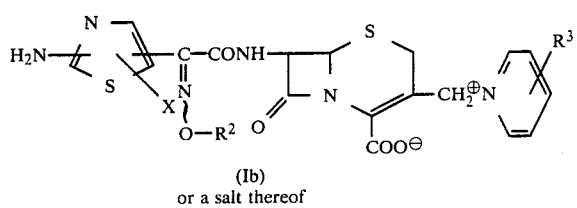

(Ib)
or a salt thereof wherein
$R^1$, $R^2$, $R^3$ and X are each as defined above;
$R^4$ is a group which can be substituted with a group of the formula:

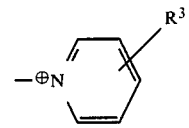

wherein $R^3$ is as defined above; and
$R_a{}^1$ is a protected amino group.

Regarding the object compound (I), (Ia) and (Ib) and the starting compound (II), it is to be understood that said object and starting compounds include syn isomer, anti isomer and a mixture thereof. For example, with regard to the object compound (I), syn isomer means one geometrical isomer having the partial structure represented by the following formula:

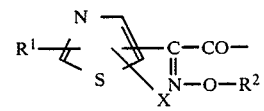

(wherein $R^1$, $R^2$ and X are each as defined above) and anti isomer means the other geometrical isomer having the partial structure represented by the following formula:

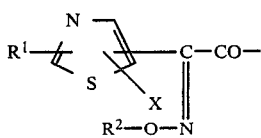

(wherein $R^1$, $R^2$ and X are each as defined above).

Regarding the other object and starting compounds, the syn and anti isomers thereof also are represented by the same geometrical configuration as that of the compound (I).

Suitable pharmaceutically acceptable salts of the object compounds (I) are conventional non-toxic salts and may include a salt with a base or an acid addition salt such as a salt with an inorganic base for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with an amino acid (e.g. aspartic acid, glutamic acid, etc.); and the like.

In the above and subsequent description of the present invention, suitable examples and illustration of the various definitions to be included within the scope thereof are explained in detail as follows.

The term "lower" in the present specification is intended to mean a group having 1 to 6 carbon atoms, unless otherwise indicated.

Suitable "amino-protective group" in the term "a protected amino group" may include conventional one which is used in penicillin and cephalosporin compounds, for example, acyl as mentioned below, mono to triphenyl(lower)alkyl (e.g. benzyl, penethyl, benzhydryl, trityl, etc.), lower alkoxycarbonyl(lower)alkylidene or its enamine tautomer (e.g. 1-methoxycarbonyl-1-propen-2-yl, etc.), di(lower)alkylaminomethylene (e.g. dimethylaminomethylene, etc.), etc.

Suitable "acyl" may include an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), ($C_3$–$C_7$)-cycloalkanecarbonyl (e.g. cyclohexanecarbonyl, etc.), and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include phenyl(lower)alkanoyl (e.g. phenylacetyl, phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituent(s) may be mono (or di or tri)halo(lower)alkanoyl (e.g. chloroacetyl, bromoacetyl, dichloroacetyl, trifluoroacetyl, etc.), mono (or di or tri)halo(lower)alkoxycarbonyl (e.g. chloromethoxycarbonyl, dichloromethoxycarbonyl, 2,2,2-tri-chloroethoxycarbonyl, etc.), nitro (or halo or lower alkoxy)phenyl(lower)alkoxycarbonyl (e.g. nitrobenzyloxycarbonyl, chlorobenzyloxycarbonyl, methoxybenzyloxycarbonyl, etc.), and the like.

The preferred embodiment of the amino-protective group thus defined is lower alkanoyl.

Suitable "lower aliphatic hydrocarbon group" in the term "lower aliphatic hydrocarbon group which may have suitable substituent(s)" may be lower alkyl (e.g. methyl, ethyl, propyl, isopropyl, butyl, isobutyl, t-butyl, pentyl, hexyl, etc.), lower alkenyl (e.g. vinyl, 1-propenyl, allyl, 1 or 2 or 3-butenyl, 1 or 2 or 3 or 4-pentyl, 1 or 2 or 3 or 4 or 5-hexenyl, etc.), lower alkenyl (e.g. ethynyl, propargyl, 1 or 2 or 3-butynyl, 1 or 2 or 3 or 4-pentynyl, 1 or 2 or 3 or 4 or 5-hexynyl, etc.), or the like.

Suitable substituent(s) in the term "lower aliphatic hydrocarbon group which may have suitable substituent(s)" may be protected carboxy group as illustrated below, carboxy, or the like.

Suitable "protected carboxy group" may include an esterified carboxy group.

Suitable "ester moiety" in "esterified carboxy group" may include lower alkyl ester (e.g. methyl ester, ethyl ester, propyl ester, isopropyl ester, butyl ester, isobutyl ester, t-butyl ester, pentyl ester, tert-pentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester, isopropylthiomethyl ester, etc), amino- and carboxy-substituted-lower alkyl ester (e.g. 2-amino-2-carboxyethyl ester, 3amino-3-carboxypropyl ester, etc.), protected amino- and protected carboxy-substituted-lower alkyl ester such as lower alkoxycarbonylamino- and mono- (or di or tri)phenyl(lower)alkoxycarbonyl-substituted-lower alkyl ester (e.g. 2-tert-butoxycarbonylamino-2-benzhydryloxycarbonylethyl ester, 3-tert-butoxycarbonylamino-3-benzhydryloxycarbonylpropyl ester, etc.), mono(or di or tri)halo(lower)alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, isobutyryloxymethyl ester, valeryloxymethyl ester, pivaloyloxymethyl ester, hexanoyloxymethyl ester, 2-acetoxyethyl ester, 2-propionyloxyethyl ester, 1-acetoxypropyl ester, etc.), lower alkanesulfonyl(lower)alkyl ester (e.g. mesylmethyl ester, 2-mesylethyl ester, etc.), ar(lower)alkyl ester which may have one or more substituent(s) such as mono(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), heterocyclic ester (e.g. phthalidyl ester, etc.), and the like.

Suitable "halogen" may be chlorine, bromine, iodine or fluorine, and preferred one is chlorine or bromine.

Suitable $R^4$ may include an acid residue such as acyloxy, halogen (e.g. chlorine, bromine, iodine or fluorine), azido or the like, wherein acyl moiety in the term "acyloxy" can be referred to the ones as exemplified above.

Preferred embodiments of the object compounds (I) are as follows.

Preferred embodiment of $R^1$ is amino or acylamino (more preferably lower alkanoylamino);

$R^2$ is lower alkyl, lower alkynyl, carboxy(lower)alkyl or esterified carboxy(lower)alkyl [more preferably lower alkoxycarbonyl(lower)alkyl];

$R^3$ is amino or acylamino (more preferably lower alkanoylamino); and

X is hydrogen or halogen (more preferably chlorine or bromine).

The processes 1 and 2 for the preparation of the object compounds (I) of the present invention are explained in detail in the following.

(1) Process 1

The object compound (I) or a salt thereof can be prepared by reacting the compound (II) or a salt thereof with the compound (III) or a salt thereof.

Suitable salt of the compound (II) can be referred to the ones as exemplified for the compound (I).

Suitable salt of the compound (III) can be referred to the acid addition salt as exemplified for the compound (I).

The present reaction may be carried out in a solvent such as water, phosphate buffer, acetone, chloroform, acetonitrile, nitrobenzene, methylene chloride, ethylene chloride, formamide, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (II) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide (e.g. sodium iodide, potassium iodide, etc.), alkali metal thiocyanate (e.g. sodium thiocyanate, potassium thiocyanate, etc.) etc.

(2) Process 2

The compound (Ib) or a salt thereof can be prepared by subjecting the compound (Ia) or a salt thereof to elimination reaction of the amino protective group.

Suitable method for this elimination reaction may include conventional one such as hydrolysis, reduction, combined methods comprising iminohalogenation and then iminoetherification, followed by hydrolysis, if necessary, and the like.

(i) For Hydrolysis:

Hydrolysis is preferably carried out in the presence of an acid.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

The acid suitable for this hydrolysis can be selected according to the kinds of the protective group to be removed, for example, this hydrolysis can preferably be applied to the amino-protective group for $R_a{}^1$ such as substituted or unsubstituted lower alkoxycarbonyl, substituted or unsubstituted lower alkanoyl.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling to at somewhat elevated temperature.

(ii) For Reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.), and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction manner can be selected according to the kinds of the protective group to be removed, for example, the chemical reduction can preferably be applied to the amino-protective group for $R_a{}^1$ such as halo(lower)alkoxycarbonyl and the like, and catalytic reduction can preferably be applied to that such as substituted or unsubstituted ar(lower)alkoxycarbonyl, and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

(iii) For combined methods comprising iminohalogenation (the first step) and then iminoetherification (the 2nd step), followed by hydrolysis (the last step), if necessary:

The first and second steps of this method are preferably carried out in an anhydrous solvent. Suitable solvent for the first step (i.e. iminohalogenation) is an aprotic solvent such as methylene chloride, chloroform, diethyl ether, tetrahydrofuran, dioxane, etc., and for the second step (i.e. iminoetherification) is usually the same as those in the above first step. These two steps are usually conducted under cooling to at ambient temperature. These two steps and the last step (i.e. hydrolysis step) are most preferably conducted in one-batch system.

Suitable iminohalogenating agents include a halogenating agent such as phosphorus halo compound (e.g. phosphorus trichloride, phosphorus pentachloride, phosphorus tribromide, phosphorus pentabromide, phosphorus oxychloride, etc.), thionyl chloride, phosgene, and the like.

Suitable iminoetherifying agent may be an alcohol such as an alkanol (e.g. methanol, ethanol, propanol, isopropanol, butanol, etc.), or the corresponding alkanol having alkoxy (e.g. 2-methoxyethanol, 2-ethoxyethanol, etc.), and alkoxide of metal such as alkali metal, alkaline earth metal (e.g. sodium methoxide, potassium ethoxide, magnesium ethoxide, lithium methoxide, etc.), and the like.

Thus obtained reaction product is, if necessary, hydrolyzed in a conventional manner. The hydrolysis is preferably carried out at ambient temperature to under cooling, and proceeds simply pouring the reaction mixture into water or a hydrophilic solvent such as alcohol (e.g. methanol, ethanol, etc.) moistened or admixed with water, and if necessary, with addition of an acid or base.

Suitable acid may include the same ones as those given in the explanation of Hydrolysis mentioned in the above item (i), and suitable base may include alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), trialkylamine (e.g. triethylamine, etc.), pyridine compound (e.g. pyridine, lutidine, picoline, etc.), quinoline, and the like.

The present invention includes, within the scope of the invention, the cases that the free carboxy group in $R^2$ and/or the protected amino group in $R^3$ are transformed into the protected carboxy group and/or free amino group during this elimination reaction and post-treatment of this elimination reaction.

It is to be noted that, in the aforementioned reactions in Processes 1 and 2 and/or the post-treatment of the reactions, in case that the starting or object compounds possess a geometrical isomer, it may occasionally be transformed into the other geometrical isomer, and such case is also included within the scope of the present invention. free carboxy group or free amino group, it may be transformed into its pharmaceutically acceptable salts by a conventional method.

The object compounds (I) and the pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compounds (I), the test data on the in vitro antimicrobial activity of a representative compound of this invention are shown in the following.

Test: In vitro Antimicrobial Activity

Test Compound:
7-[2-Methoxyimino-2-(2-aminothiazol-4-yl)acetamido]-3-(3-amino-1-pyridiniomethyl)-3-cephem-4-carboxylate (syn isomer).
(hereinafter referred to as Compound A)
Test Method:

In vitro Antimicrobial activity was determined by the two-fold agar-plate dilution method as described below.

One loopful of an overnight culture of each test strain in Tripticase-soy broth (approximately $10^8$ viable cells per ml) was streaked on heart infusion agar (HI-agar) containing graded concentrations of an antimicrobial agent, and the minimal inhibitory concentration (MIC) was expressed in term of $\mu g/ml$ after incubation at 37° C. for 20 hours.

Test Results

| | MIC ($\mu g/ml$) |
| --- | --- |
| Microorganisms | Test compound Compound A |
| E. coli NIHJ JC - 2 | <0.025 |
| E. coli 31 | <0.025 |
| K. pneumoniae 20 | <0.025 |

For therapeutic administration, the object compounds (I) and the pharmaceutically acceptable salts thereof of the present invention are used in the form of conventional pharmaceutical preparation which contains said compound, as active ingredients, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like. If needed, there may be included in the above preparations auxiliary substances, stabilizing agents, wetting agents and other commonly used additives such as lactose, magnesium stearate, terra alba, sucrose, corn starch, talc, stearic acid, gelatin, agar, pectin, peanut oil, olive oil, cacao butter, ethyleneglycol and the like.

While the dosage of the compounds (I) may vary from and also depend upon the age, conditions of the patient, a kind of diseases, a kind of the compounds (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compounds (I) of the present invention may be used in treating diseases infected by pathogenic microorganisms.

The following preparations and examples are given for the purpose of illustrating the present invention.

Preparation 1

To a Vilsmeier reagent [prepared from phosphorus oxychloride (16.0 g) and N,N-dimethylformamide (7.63 g) in a usual manner] in ethyl acetate (190 ml) was added 2-t-butoxycarbonylmethoxyimino-2-(2-formamidothiazol-4-yl)acetic acid (syn isomer) (19.09 g) at 5° C. under cooling in an ice bath and stirring, which was continued for 40 minutes at 5° to 8° C. to give an activated acid solution. On the other hand, a mixture of 7-aminocephalosporanic acid (17.71 g) and trimethylsilylacetamide (61 g) in methylene chloride (260 ml) was stirred at room temperature to make a solution and cooled to −20° C. To the cold solution was added the above activated acid solution and the mixture was stirred for 40 minutes at −12° to −8° C. The reaction mixture was poured into an aqueous solution (400 ml) of sodium bicarbonate (40 g) and evaporated to remove methylene chloride. The aqueous solution was washed with ethyl acetate, adjusted to pH 3 with 6N hydrochloric acid and extracted with ethyl acetate. The extract was washed with brine, dried over magnesium sulfate, treated with charcoal and evaporated. The wet residue was triturated in diisopropyl ether to give 7-[2-t-butoxycarbonylmethoxyimino-2-(2-formamidothiazol-4-yl)acetamido]cephalosporanic acid (syn isomer) (33.85 g), mp 85° to 90° C.

IR (Nujol): 3450, 3250, 1785, 1730, 1680, 1540 cm$^{-1}$

NMR (DMSO-d$_6$, δ): 1.45 (9H, s), 2.03 (3H, s), 3.60 (2H, m), 4.62 (2H, s), 4.67 and 5.07 (2H, ABq, J=14 Hz), 5.20 (1H, d, J=5 Hz), 5.85 (1H, dd, J=5 and 8 Hz), 7.43 (1H, s), 8.49 (1 H, s), 9.55 (1H, d, J=8 Hz)

Preparation 2

The following compounds were obtained according to a similar manner to that of Preparation 1.

(1) 7-[2-Propargyloxyimino-2-(2-formamidothiazol-4-yl)acetamido]cephalosporanic acid (syn isomer), mp 85° to 90° C. (dec.).

IR (Nujol): 3450, 3250, 3050, 1780, 1720, 1670, 1650, 1540 cm$^{-1}$

NMR (DMSO-d$_6$, δ): 2.00 (3H, s), 3.43 (1H, t, J=2 Hz), 3.55 (2H, broad s), 4.73 (2H, d, J=2 Hz), 4.77 and 5.12 (2H, ABq, J=13 Hz), 5.18 (1H, d, J=5 Hz), 5.78 (1H, dd, J=5 and 8 Hz), 7.40 (1H, s), 8.47 (1H, s), 9.70 (1H, d, J=8 Hz), 12.57 (1H, broad s)

(2) 7-[2-Methoxyimino-2-(2-formamido-5-chlorothiazol-4-yl)acetamido]cephalosporanic acid (syn isomer), mp 155° to 159° C. (dec.).

IR (Nujol): 3500, 3200, 3050, 1780, 1740, 1680, 1650, 1540 cm$^{-1}$

NMR (DMSO-d$_6$, δ): 2.03 (3H, s), 3.57 (2H, broad s), 3.93 (3H, s), 4.68 and 5.05 (2H, ABq, J=13 Hz), 5.17 (1H, d, J=5 Hz), 5.83 (1H, dd, J=5 and 8 Hz), 8.52 (1H, s), 9.63 (1H, d, J=8 Hz), 12,85 (1H, broad s)

Preparation 3

A mixture of 7-[2-t-butoxycarbonylmethoxyimino-2-(2-formamidothiazol-4-yl)acetamido]cephalosporanic acid (syn isomer) (19 g) and anisole (23 ml) in trifluoroacetic acid (123 ml) was stirred for 50 minutes at room temperature. The solvent was evaporated and the residue was dissolved in a mixture of ethyl acetate and aqueous solution of sodium bicarbonate.

The mixture was adjusted to pH 4 with 1N hydrochloric acid and the aqueous layer was separated out. To the aqueous solution was added ethyl acetate and the mixture was adjusted to pH 1.5 with 1N hydrochloric acid and then extracted with ethyl acetate. The extract was washed with brine, dried over magnesium sulfate, treated with charcoal and evaporated to dryness. The residue was triturated in diethyl ether to give 7-[2-carboxymethoxyimino-2-(2-formamidothiazol-4-yl)acetamido]cephalosporanic acid (syn isomer) (7.8 g), mp 80° to 85° C.

IR (Nujol): 3500, 3200, 1770, 1750-1630, 1540 cm$^{-1}$

NMR (DMSO-d$_6$+D$_2$O, δ): 2.03 (3H, s), 3.57 (2H, m), 4.70 (2H, s), 4.73 and 4.97 (2H, ABq, J=14 Hz), 5.18 (1H, d, J=5 Hz), 5.87 (1H, d, J=5 Hz), 7.47 (1H, s), 8.50 (1H, s)

EXAMPLE 1

A mixture of 7-[2-methoxyimino-2-(2-formamidothiazol-4-yl)acetamido]cephalosporanic acid (syn isomer) (10.15 g), 3-formamidopyridine (4.7 g), sodium iodide (37.2 g), phosphoric acid (1.24 g), sodium bicarbonate (1.77 g), water (6.3 ml) and acetonitrile (19 ml) was stirred for 1.5 hours at 70° to 75° C. The reaction mixture was diluted with water (200 ml), adjusted to pH 3 with 6N hydrochloric acid and washed with ethyl acetate. The aqueous solution was evaporated to remove ethyl acetate and subjected to column chromatography on a non ionic adsorption resin "Diaion HP-20" (Trademark: Prepared by Mitsubishi Chemical Industries) (305 ml). After the column was washed with water, the elution was carried out with 30% aqueous methanol. The fractions containing an object compound were collected, evaporated to remove methanol under reduced pressure and lyophilized to give 7-[2-methoxyimino-2-(2-formamidothiazol-4-yl)acetamido]-3-(3-formamido-1-pyridiniomethyl)-3-cephem-4-carboxylate (syn isomer) (5.14 g), mp 157° to 163° C. (dec.).

IR (Nujol): 3200, 1770, 1670, 1600, 1540, 1500 cm$^{-1}$

NMR (D$_2$O+CD$_3$OD, δ): 3.20 and 3.72 (2H, ABq, J=18 Hz), 3.96 (3H, s), 5.26 (1H, d, J=5 Hz), 5.30 and 5.62 (2H, ABq, J=14 Hz), 5.84 (1H, d, J=5 Hz), 7.36 (1H, s), 8.0 (1H, m), 8.40 (1H, s), 8.48 (1H, s), 8.20–8.56 (1H, m), 8.72 (1H, m), 9.48 (1H, s)

EXAMPLE 2

The following compounds were obtained according to a similar manner to that of Example 1.

(1) 7-[2-Carboxymethoxyimino-2-(2-formamidothiazol-4-yl)acetamido]-3-(3-formamido-1-pyridiniomethyl)-3-cephem-4-carboxylate (syn isomer), mp 160° to 165° C. (dec.).

IR (Nujol): 3200, 3100, 1780, 1720-1660, 1590, 1580-1520, 1500 cm$^{-1}$

NMR (DMSO-d$_6$, δ): 3.15 and 3.65 (2H, ABq, J=18 Hz), 4.63 (2H, broad s), 5.15 (1H, d, J=5 Hz), 5.25 and 5.70 (2H, ABq, J=14 Hz), 5.80 (1H, d, J=5 Hz), 7.43

(1H, s), 7.90–8.23 (1H, m), 8.50 (1H, s(, 8.33–8.77 (2H, m), 8.90 (1H, m), 9.45 (1H, broad s)

(2) 7-[2-Carboxymethoxyimino-2-(2-aminothiazol-4-yl)acetamido]-3-(3-amino-1-pyridiniomethyl)-3-cephem-4-carboxylate (syn isomer), mp 189° to 193° C. (dec.).

IR (Nujol): 3300, 3200, 1770, 1670-1560, 1530, 1510 $cm^{-1}$ (3) 7-[2-Methoxycarbonylmethoxyimino-2-(2-aminothiazol-4-yl)acetamido]-3-(3-amino-1-pyridiniomethyl)-3-cephem-4-carboxylate (syn isomer), mp 171° to 175° C. (dec.).

IR (Nujol): 3300, 3100, 1770, 1670-1590, 1540, 1510 $cm^{-1}$ (4) 7-[2-Propargyloxyimino-2-(2-formamidothiazol-4-yl)acetamido]-3-(3-formamido-1-pyridiniomethyl)-3-cephem-4-carboxylate (syn isomer), mp 159° to 163° C. (dec.).

IR (Nujol): 3250, 1770, 1670, 1600, 1550, 1500 $cm^{-1}$

NMR (DMSO-$d_6$+$D_2O$, δ): 3.03–3.83 (2H, m), 3.42 (1H, t, J=2 Hz), 4.80 (2H, m), 5.15 (1H, d, J=5 Hz), 5.28 and 5.78 (2H, ABq, J=14 Hz), 5.78 (1H, d, J=5 Hz), 7.47 (1H, s), 7.93–8.43 (1H, m), 8.53 (1H, s), 8.40–8.87 (2H, m), 9.03 (1H, m), 9.57 (1H, broad s)

(5) 7-[2-Propargyloxyimino-2-(2-aminothiazol-4-yl)acetamido]-3-(3-amino-1-pyridiniomethyl)-3-cephem-4-carboxylate (syn isomer), mp 175° to 180° C. (dec.).

IR (Nujol): 3500-3200, 1770, 1660-1590, 1540, 1510 $cm^{-1}$ (6) 7-[2-Methoxyimino-2-(2-aminothiazol-4-yl)acetamido]-3-(3-amino-1-pyridiniomethyl)-3-cephem-4-carboxylate (syn isomer), mp 185° to 189° C. (dec.).

IR (Nujol): 3300, 3200, 1770, 1670-1580, 1530, 1510 $cm^{-1}$ (7) 7-[2-Methoxyimino-2-(2-amino-5-chlorothiazol-4-yl)acetamido]-3-(3-amino-1-pyridiniomethyl)-3-cephem-4-carboxylate (syn isomer), mp 168° to 172° C. (dec.).

IR (Nujol): 3350, 3200, 3050, 1770, 1680-1580, 1540, 1510 $cm^{-1}$ (8) 7-[2-Methoxyimino-2-(2-formamido-5-chlorothiazol-4-yl)acetamido]-3-(3-formamido-1-pyridiniomethyl)-3-cephem-4-carboxylate (syn isomer), mp 153° to 157° C. (dec.).

IR (Nujol): 3500, 3200, 3050, 1780, 1680, 1610, 1550, 1500 $cm^{-1}$

NMR (DMSO-$d_6$+$D_2O$, δ): 3.12 and 3.62 (2H, ABq, J=18 Hz), 3.88 (3H, s), 5.10 (1H, d, J=5 Hz), 5.10–5.87 (2H, m), 5.75 (1H, d, J=5 Hz), 7.90–8.38 (1H, m), 8.43–8.80 (1H, m), 8.50 (2H, broad s), 8.98 (1H, m), 9.50 (1H, broad s)

EXAMPLE 3

A mixture of 7-[2-carboxymethoxyimino-2-(2-formamidothiazol-4-yl)acetamido]-3-(3-formamido-1-pyridiniomethyl)-3-cephem-4-carboxylate (syn isomer) (1.8 g) and conc. hydrochloric acid (0.9 ml) in methanol (18 ml) was stirred for 3 hours at room temperature and evaporated to dryness. The residue was dissolved in water (50 ml) and subjected to column chromatography on a non ionic adsorption resin "Diaion HP 20" (90 ml). After the column was washed with water, the elution was carried out with 20%, 30% and 40% aqueous methanol. First fractions containing 7-[2-carboxymethoxyimino-2-(2-aminothiazol-4-yl)acetamido]-3-(3-amino-1-pyridiniomethyl)-3-cephem-4-carboxylate (syn isomer) were collected, evaporated to remove methanol under reduced pressure and lyophilized to give the said compound (180 mg), mp 189° to 193° C. (dec.).

IR (Nujol): 3300, 3200, 1770, 1670-1560, 1530, 1510 $cm^{-1}$

NMR ($D_2O$+NaHCO$_3$, δ): 3.08 and 3.58 (2H, ABq, J=18 Hz), 4.53 (2H, s), 5.23 (1H, d, J=5 Hz), 5.03–5.73 (2H, m), 5.80 (1H, d, J=5 Hz), 6.90 (1H, s), 7.62 (2H, m), 8.02 (1H, m), 8.12 (1H, broad s)

the second fractions containing 7-[2-methoxycarbonylmethoxyimino-2-(2-aminothiazol-4-yl)acetamido]-3-(3-amino-1-pyridiniomethyl)-3-cephem-4-carboxylate (syn isomer) were treated by the same manner as mentioned above to give a powder (580 mg). The powder (500 mg) was dissolved in an aqueous solution of sodium bicarbonate, adjusted to pH 4.5 with 1N hydrochloric acid and subjected to column chromatography on a non ionic adsorption resin "Diaion HP-20" (25 ml). After the column was washed with water and 20% aqueous methanol, the elution was carried out with 30% and 40% aqueous methanol. The eluates were evaporated to remove methanol under reduced pressure and lyophilized to give 7-[2-methoxycarbonylmethoxyimino-2-(2-aminothiazol-4-yl)acetamido]-3-(3-amino-1-pyridiniomethyl)-3-cephem-4-carboxylate (syn isomer) (230 mg), mp 171° to 175° C. (dec.).

IR (Nujol): 3300, 3200, 1770, 1670-1590, 1540, 1510 $cm^{-1}$

NMR (DMSO-$d_6$+$D_2O$, δ): 2.95 and 3.48 (2H, ABq, J=18 Hz), 3.63 (3H, s), 4.60 (2H, s), 5.02 (1H, d, J=5 Hz), 4.77–5.50 (2H, m), 5.63 (1H, d, J=5 Hz), 6.72 (1H, s), 7.58 (2H, m), 8.23 (1H, m), 8.40 (1H, broad s)

EXAMPLE 4

A mixture of 7-[2-methoxyimino-2-(2-formamidothiazol-4-yl)acetamido]-3-(3-formamido-1-pyridiniomethyl)-3-cephem-4-carboxylate (syn isomer) (4.4 g) and conc. hydrochloric acid (1.6 ml) in methanol was stirred for 4 hours at room temperature and evaporated to dryness. The residue was dissolved in water (100 ml) and subjected to column chromatography on a non ionic adsorption resin "Diaion HP 20" (160 ml). After the column was washed with water, the elution was carried out with 20% aqueous methanol. The fractions containing an object compound were collected, evaporated to remove methanol under reduced pressure and lyophilized to give 7-[2-methoxyimino-2-(2-aminothiazol-4-yl)acetamido]-3-(3-amino-1-pyridiniomethyl)-3-cephem-4-carboxylate (syn isomer) (2.3 g), mp 185° to 189° C. (dec.).

IR (Nujol): 3300, 3200, 1770, 1670-1580, 1530, 1510 $cm^{-1}$

NMR ($D_2O$+CD$_3$OD, δ): 3.10 and 3.65 (2H, ABq, J=18 Hz), 3.95 (3H, s), 5.10 and 5.48 (2H, ABq, J=14 Hz), 5.23 (1H, d, J=5 Hz), 5.83 (1H, d, J=5 Hz), 6.87 (1H, s), 7.70 (2H, m), 8.15 (1H, m), 8.30 (1H, broad s)

EXAMPLE 5

The following compounds were obtained according to a similar manner to that of Example 4.

(1) 7-[2-Methoxycarbonylmethoxyimino-2-(2-aminothiazol-4-yl)acetamido]-3-(3-amino-1-pyridiniomethyl)-3-cephem-4-carboxylate (syn isomer), mp 171° to 175° C. (dec.).

IR (Nujol): 3300, 3200, 1770, 1670-1590, 1540, 1510 $cm^{-1}$ (2) 7-[2-Propargyloxyimino-2-(2-aminothiazol-4-yl)acetamido]-3-(3-amino-1-pyridiniomethyl)-3-cephem-4-carboxylate (syn isomer), mp 175° to 180° C. (dec.).

IR (Nujol): 3500-3200, 1770, 1660-1590, 1540, 1510 cm$^{-1}$

NMR (DMSO-d$_6$+D$_2$O, δ): 3.23 and 3.68 (2H, ABq, J=18 Hz), 3.45 (1H, t, J=2 Hz), 4.82 (2H, m), 5.20 (1H, d, J=5 Hz), 5.13 and 5.62 (2H, ABq, J=14 Hz), 5.82 (1H, d, J=5 Hz), 6.90 (1H, s), 7.75 (2H, m), 8.37 (1H, m), 8.53 (1H, m)

(3) 7-[2-Methoxyimino-2-(2-amino-5-chlorothiazol-4-yl)acetamido]-3-(3-amino-1-pyridiniomethyl)-3-cephem-4-carboxylate (syn isomer), mp 168° to 172° C. (dec.).

IR (Nujol): 3350, 3200, 3050, 1770, 1680-1580, 1540, 1510 cm$^{-1}$

NMR (DMSO-d$_6$+D$_2$O, δ): 3.10 and 3.12 (2H, ABq, J=18 Hz), 3.88 (3H, s), 5.13 (1H, d, J=5 Hz), 4.93–5.70 (2H, m), 5.77 (1H, d, J=5 Hz), 7.70 (2H, m), 8.33 (1H, m), 8.47 (1H, broad s)

What is claimed is:

1. A compound of the formula:

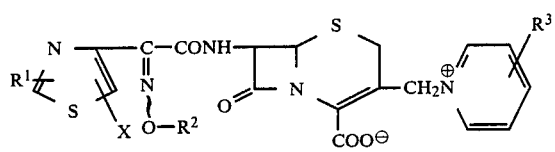

wherein

R$^1$ is amino or lower alkanoylamino,

R$^2$ is lower alkyl, lower alkynyl, carboxy(lower)alkyl or esterified carboxy(lower)alkyl, R$^3$ is amino or lower alkanoylamino, and X is hydrogen or halogen; and pharmaceutically acceptable salts thereof.

2. Syn isomer of a compound of claim 1, wherein

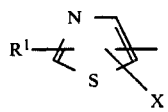

group is

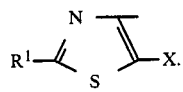

3. A compound of claim 2, wherein

R$^1$ is amino or lower alkanoylamino,

R$^2$ is lower alkyl, lower alkynyl, carboxy(lower)alkyl or lower alkoxycarbonyl(lower)alkyl, and R$^3$ is amino or lower alkanoylamino.

4. A compound of claim 3, wherein

R$^1$ is amino or formamido,

R$^2$ is methyl, propargyl, carboxymethyl or methoxycarbonylmethyl,

R$^3$ is amino or formamido, and

X is hydrogen.

5. A compound of claim 4, which is selected from the group consisting of:

7-[2-carboxymethoxyimino-2-(2-aminothiazol-4-yl)acetamido]-3-(3-amino-1-pyridiniomethyl)-3-cephem-4-carboxylate (syn isomer), 7-[2-methoxycarbonylmethoxyimino-2-(2-aminothiazol-4-yl)acetamido]-3-(3-amino-1-pyridiniomethyl)-3-cephem-4-carboxylate (syn isomer), 7-[2-methoxyimino-2-(2-aminothiazol-4-yl)acetamido]-3-(3-amino-1-pyridiniomethyl)-3-cephem-4-carboxylate (syn isomer) and 7-[2-propargyloxyimino-2-(2-aminothiazol-4-yl)acetamido]-3-(3-amino-1-pyridiniomethyl)-3-cephem-4-carboxylate (syn isomer).

6. A compound of claim 3, wherein

R$^1$ is amino or formamido,

R$^2$ is methyl,

R$^3$ is amino or formamido, and

X is chlorine.

7. A compound of claim 6, which

7-[2-methoxyimino-2-(2-amino-5-chlorothiazol-4-yl)acetamido]-3-(3-amino-1-pyridiniomethyl)-3-cephem-4-carboxylate (syn isomer).

8. A pharmaceutical antibacterial composition comprising, as an active ingredient, an effective amount of the compound of claim 1, in association with a non-toxic, pharmaceutically acceptable carrier or excipient.

9. A method for the treatment of bacterial infections which comprises administering to a human being or animal a pharmaceutical antibacterial composition comprising, as an active ingredient, an effective amount of the compound of claim 1, in association with a non-toxic, pharmaceutically acceptable carrier or excipient.

* * * * *